United States Patent [19]

Mapp

[11] 4,033,347
[45] July 5, 1977

[54] DISPOSABLE SYRINGE

[76] Inventor: Calvin R. Mapp, 1125 NW. 88th St., Miami, Fla. 33150

[22] Filed: Apr. 5, 1976

[21] Appl. No.: 673,900

[52] U.S. Cl. .............................. 128/227; 128/251
[51] Int. Cl.² ........................................ A61M 3/00
[58] Field of Search ........................... 128/227, 251

[56] References Cited

UNITED STATES PATENTS

| | | | |
|---|---|---|---|
| 655,744 | 8/1900 | Valentine | 128/227 |
| 718,202 | 1/1903 | Hardman, Jr. | 128/227 |
| 1,089,980 | 3/1914 | Strayer | 128/227 X |
| 1,154,627 | 9/1915 | Hall | 128/227 |
| 1,233,117 | 7/1917 | Parker | 128/227 X |
| 1,901,069 | 3/1933 | Williams | 128/227 |
| 2,612,161 | 9/1952 | Manville | 128/227 |
| 3,100,487 | 8/1963 | Bathish | 128/227 |
| 3,476,111 | 11/1969 | Matheson | 128/227 |

Primary Examiner—John D. Yasko
Attorney, Agent, or Firm—Allen D. Brufsky

[57] ABSTRACT

A disposable syringe for vaginal douching including a ring and a collapsible bag depending from the ring. The ring has an integral hook for hanging the bag on a convenient support in a bathroom. A threaded, tubular connector on a side wall of the bag receives the threaded end of a douche hose.

4 Claims, 2 Drawing Figures

DISPOSABLE SYRINGE

BACKGROUND OF THE INVENTION

This invention relates to a syringe, and more particularly to a disposable syringe for vaginal douche purposes.

There is a recognized need for a single-use, disposable vaginal douche or syringe because of the difficulty in keeping reuseable syringes sterile and sanitary. Furthermore, such devices should be available at a nominal cost, so that they can be sold in vending machines in women's rest rooms and discarded after use, whereby a necessary article of feminine hygiene can be rendered available to women travelling or away from home. In such instances, the syringe should be provided with means to readily enable its use in the bathroom of a hotel or motel.

SUMMARY OF THE INVENTION

Accordingly, it is an object of this invention to provide a disposable syringe for use in vaginal douching which is collapsible for ready and easy carrying and vending.

A further object of this invention is to provide a disposable syringe of the character indicated provided with an integral hook for hanging the syringe on the top of a shower door or a shower rod in a bathroom.

Yet another object of this invention is to provide an inexpensive, disposable syringe of the character indicated which can be compacted and sold as a kit.

The disposable syringe consists of an integral ring, collapsible bag, and hook, the bag depending from the ring and the hook being attached to the ring, whereby the bag may be filled with a liquid and hung from a convenient support, and a length of flexible hose adapted to be connected to a side wall of the bag.

BRIEF DESCRIPTION OF THE DRAWING

Further objects and advantages of the invention will become more apparent from the following description and claims, and from the accompanying drawing, wherein:

DETAILED DESCRIPTION OF THE PREFERRED EMBODIMENT

Figure 1:
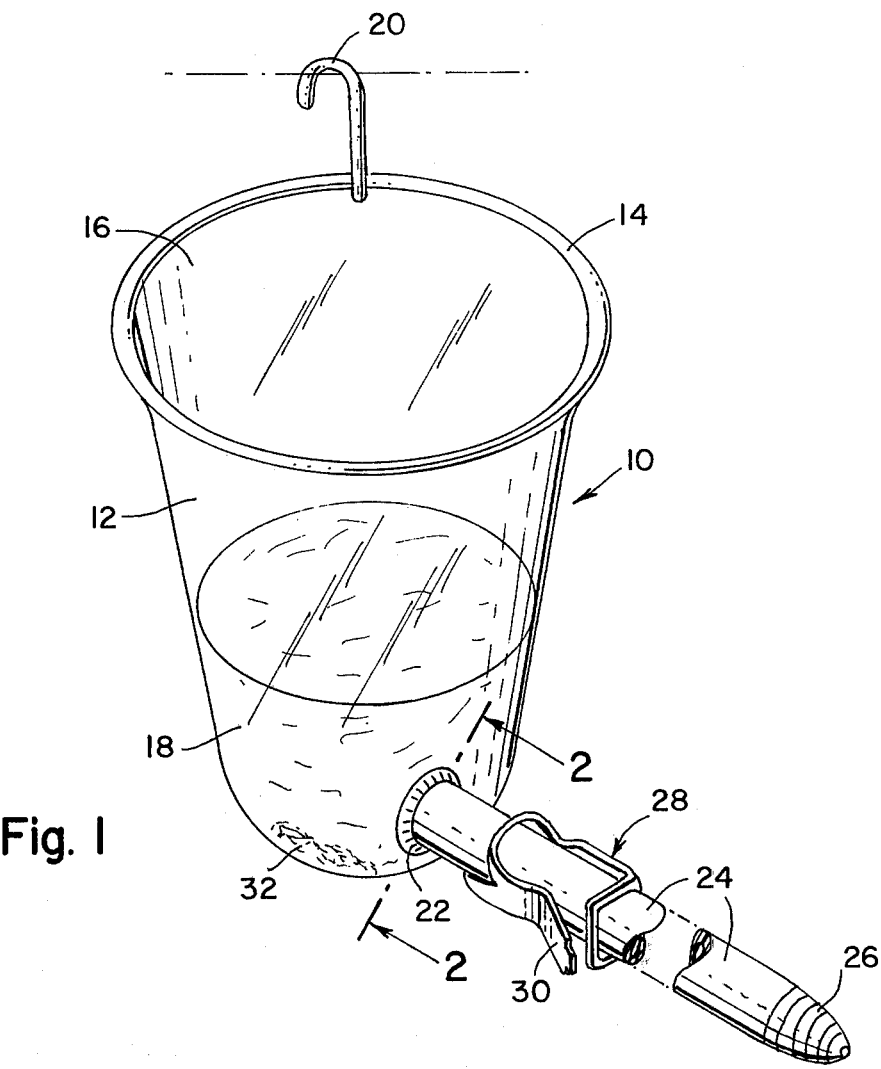
FIG. 1 is a perspective view of the disposable syringe of the present invention in assembled form.
Figure 2:
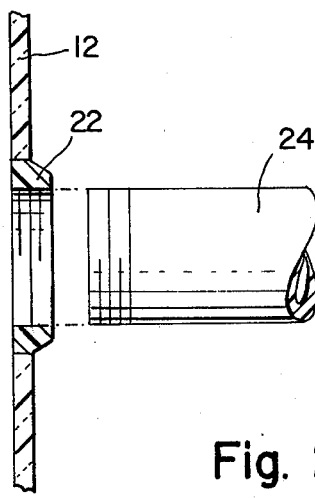
FIG. 2 is a cross-sectional view taken substantially along the plane indicated by line 2—2 of FIG. 1.

Referring now to the drawing in detail, wherein like numerals indicate like elements throughout the several views, the disposable syringe 10 of the present invention includes a collapsible clear plastic bag 12 depending from a rigid plastic ring 14 forming a mouth 16 for bag 12 through which water 18 or water and douche mixture is inserted in bag 12. Bag 12 may be collapsed against ring 14 for packaging purposes.

A plastic hook 20 is molded integral with ring 14 and may be used to hang bag 12 from the top of a shower door or from a shower rod in a bathroom.

The sidewall of bag 12 is provided with an integral tubular connector 22 whose interior is threaded to receive the threaded end of a length of a flexible douche hose 24 having a tip 26 insertable into the vagina of the user. A clamp 28 is positioned on hose 24 intermediate its ends so that when end 30 is depressed, the supply of water 18 through hose 24 can be stopped by pinching hose 24 between opposite sides of clamp 28.

Integral bag 12, ring 14, hook 20 and connector 22 are collapsed and packaged with hose 24 and clamp 28. Bag 12 can be removed from the package when needed and hose 24 connected. Bag 12 is then filled with water 18 and hung by hook 20 from a convenient place and syringe 10 is ready for use. Any sediment material 32 in the water 18 will face to the bottom of bag 12, rather than being dispersed through hose 24. When use of bag 12 is finished, the entire syringe 10 may be thrown away.

I claim:

1. A disposable syringe comprising:
    a ring, collapsible bag, and a u-shaped hook, said ring and said hook being of unitary construction, said bag depending from said ring, said ring forming the mouth of said bag, whereby said bag may be filled with a liquid and hung by said hook from a convenient support, and
    a length of flexible hose adapted to be connected to a side wall of said bag and a tubular connector on the sidewall of said bag for receiving said flexible hose, one end of said flexible hose including a contoured tip for insertion into a body cavity.

2. A disposable syringe in accordance with claim 1, wherein said tubular connector is threaded.

3. A disposable syringe in accordance with claim 2 including
    clamp means on said flexible hose intermediate its ends for compressing said hose to stop the flow of liquid from said bag through said hose.

4. A disposable syringe in accordance with claim 1 wherein said bag is formed from clear plastic material.

* * * * *